United States Patent
Hu et al.

(10) Patent No.: US 7,872,233 B2
(45) Date of Patent: Jan. 18, 2011

(54) THERMO-OPTIC INFRARED PIXEL AND FOCAL PLANE ARRAY

(75) Inventors: Juejun Hu, Cambridge, MA (US);
Ning-Ning Feng, Somerville, MA (US);
Anuradha M. Agarwal, Weston, MA (US); Lionel C. Kimerling, Concord, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 144 days.

(21) Appl. No.: 12/361,079

(22) Filed: Jan. 28, 2009

(65) Prior Publication Data

US 2010/0187419 A1 Jul. 29, 2010

(51) Int. Cl.
*G01J 5/00* (2006.01)
(52) U.S. Cl. .............. 250/338.1; 250/340; 359/254; 359/321; 359/345
(58) Field of Classification Search .............. 250/338.1, 250/340; 359/321, 254, 345
See application file for complete search history.

(56) References Cited

U.S. PATENT DOCUMENTS

| | | | |
|---|---|---|---|
| 4,915,482 A | 4/1990 | Collins et al. | |
| 4,959,546 A | 9/1990 | Bly | |
| 4,994,672 A | 2/1991 | Cross et al. | |
| 5,815,278 A * | 9/1998 | Johnston et al. | 356/445 |
| 6,034,809 A | 3/2000 | Anemogiannis | |
| 6,770,882 B2 | 8/2004 | Carr et al. | |
| 2005/0275934 A1 | 12/2005 | Ballato et al. | |
| 2007/0289623 A1 | 12/2007 | Atwater | |
| 2010/0128272 A1 * | 5/2010 | Zong et al. | 356/445 |

FOREIGN PATENT DOCUMENTS

| | | |
|---|---|---|
| JP | 2008176209 | 7/2008 |
| WO | 2008072688 | 6/2008 |

OTHER PUBLICATIONS

Notification of Transmittal of the International Search Report and the Written Opinion of the International Searching Authority mailed Aug. 20, 2010 in connection with PCT/US2010/021916.

* cited by examiner

*Primary Examiner*—David P Porta
*Assistant Examiner*—Djura Malevic
(74) *Attorney, Agent, or Firm*—Gauthier & Connors LLP

(57) ABSTRACT

A surface plasmon polariton (SPP) pixel structure is provided. The SPP pixel structure includes a coupling structure that couples the probing light into the SPP mode by matching the in-plane wave vector by changing the refractive index of the coupling structure using thermo-optic effects to vary the coupling strength of the probing light into the SPP mode. An absorber layer is positioned on the coupling structure for absorbing incident infrared/thermal radiation being detected.

25 Claims, 5 Drawing Sheets

THERMO-OPTIC INFRARED PIXEL AND FOCAL PLANE ARRAY

BACKGROUND OF THE INVENTION

The invention is related to the field of thermal infrared detectors, and in particular to thermal infrared detectors having infrared (IR) pixel designs that utilize thermo-optic effect to detect thermal radiation.

Thermal infrared detectors basically work by measuring temperature changes induced by incident infrared radiation (especially mid-IR to far-IR wavelength in the range of 2-25 µm). A number of physical quantities that show temperature dependence have been quantified for infrared detection and have been realized in focal plane array designs. Such examples include electrical resistance (vanadium oxide, amorphous silicon or polycrystalline germanium bolometers), pyroelectric effect (pyroelectric pile) and thermal expansion (thermal bimorph). Despite the variety of detection mechanisms, a typical thermal detector pixel is comprised of two components—the infrared absorption part which absorbs incident radiation; and the transduction part that converts the temperature change resulting from absorbed light into a measurable physical quantity that can be read out and processed.

SUMMARY OF THE INVENTION

According to one aspect of the invention, there is provided a surface plasmon polariton (SPP) pixel structure. The SPP pixel structure includes a coupling structure couples the probing light into the SPP mode by matching the in-plane wave vector by changing the refractive index of the coupling structure using thermo-optic effects to vary the coupling strength of the probing light into the SPP mode. An absorber layer is positioned on the coupling structure for absorbing incident infrared/thermal radiation being detected.

According to another aspect of the invention, there is provided a method of forming a surface plasmon polariton (SPP) pixel structure. The method includes positioning that couples the probing light into the SPP mode by matching the in-plane wave vector by changing the refractive index of the coupling structure using thermo-optic effects to vary the coupling strength of the probing light into the SPP mode. Moreover, the method includes positioning an absorber layer on the coupling structure for absorbing incident infrared/thermal radiation being detected.

According to another aspect of the invention, there is provided a surface plasmon polariton (SPP) focal plan array (FPA). The SPP FPA includes a plurality of surface plasmon polariton (SPP) pixel structures used in the formation of a thermal image. Each of the SPP pixel structures includes a coupling structure that couples the probing light into the SPP mode by matching the in-plane wave vector by changing the refractive index of the coupling structure using thermo-optic effects to vary the coupling strength of the probing light into the SPP mode. An absorber layer is positioned on the coupling structure for absorbing incident infrared/thermal radiation being detected.

DETAILED DESCRIPTION OF THE INVENTION

The invention utilizes thermo-optic effect (modification of material refractive index in response to temperature change) combined with highly sensitive index measurement mechanisms for infrared detection. Compared to thermal expansion (typical thermal expansion coefficient of materials: $10^{-6}$ to $10^{-5}$/K), the thermo-optic effect, in certain materials such as semiconductors, polymers and liquid crystals, shows much stronger temperature dependence with a typical thermo-optic coefficient of $10^{-4}$ to $10^{-3}$/K. Furthermore, the refractive index measurement technologies used by the invention, such as surface plasmon polariton (SPP) and photonic crystal resonance (PCR), are capable of tracing very small index changes and thus highly efficient infrared radiation detection can be achieved.

Another major advantage of the pixels described in this invention is the low fabrication cost, due to the robust pixel structures made of reliable materials monolithically integrated onto a Si-based platform based on CMOS processing. Mature CMOS technology also makes it possible for higher FPA spatial resolution and large area array processing, both of which present challenges to traditional hybrid thermal FPA architecture. In addition, the optical readout scheme inherent in the inventive pixel design provides competitive advantages over electrical readout (employed by bolometers) because of its high thermal isolation and low noise characteristics. This type of optical readout design eliminates the need to integrate electronic readout circuitry with the pixels, and can be readily replaced at low cost, if damaged or contaminated, while preserving the costly optical imaging system.

Several examples for the infrared pixel designs are herein formed in accordance with the invention. Two typical device schemes, in which 1) surface plasmon polariton (SPP) measurement, and 2) guided photonic crystal resonance (PCR) in photonic crystal slab measurement are utilized for infrared detection, are sketched below. Nevertheless, the scope of the invention is not limited to the specific designs and applications.

The thermo-optic infrared detection is achieved by monitoring surface plasmon polariton coupling strength. The surface plasmon polariton coupling strength is very sensitive to refractive index changes near the metal surface. Similarly, the coupling strength to guided photonic crystal resonance is also very sensitive to changes in the slab index. Thus index change due to thermo-optic effect can be detected through a probing light via monitoring its: 1) coupling angle; 2) coupling wavelength or 3) intensity of reflected/transmitted beam.

Figure 1A:
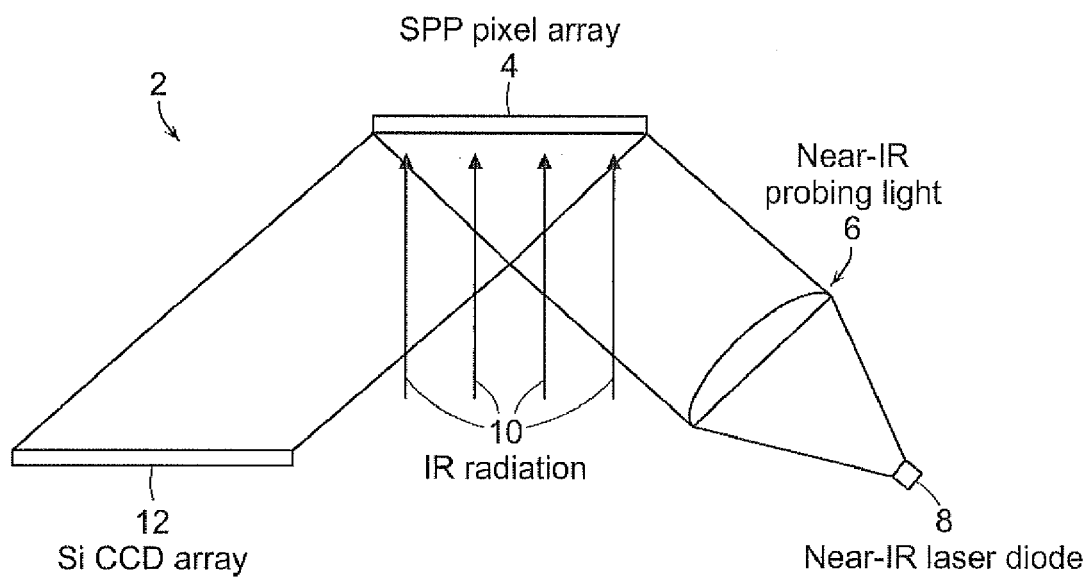
FIGS. 1A and 1B are a schematic diagrams illustrating two optical designs of surface plasmon polariton (SPP)/photonic crystal slab infrared focal plane array (FPA) used in accordance with the invention.
Figure 1B:
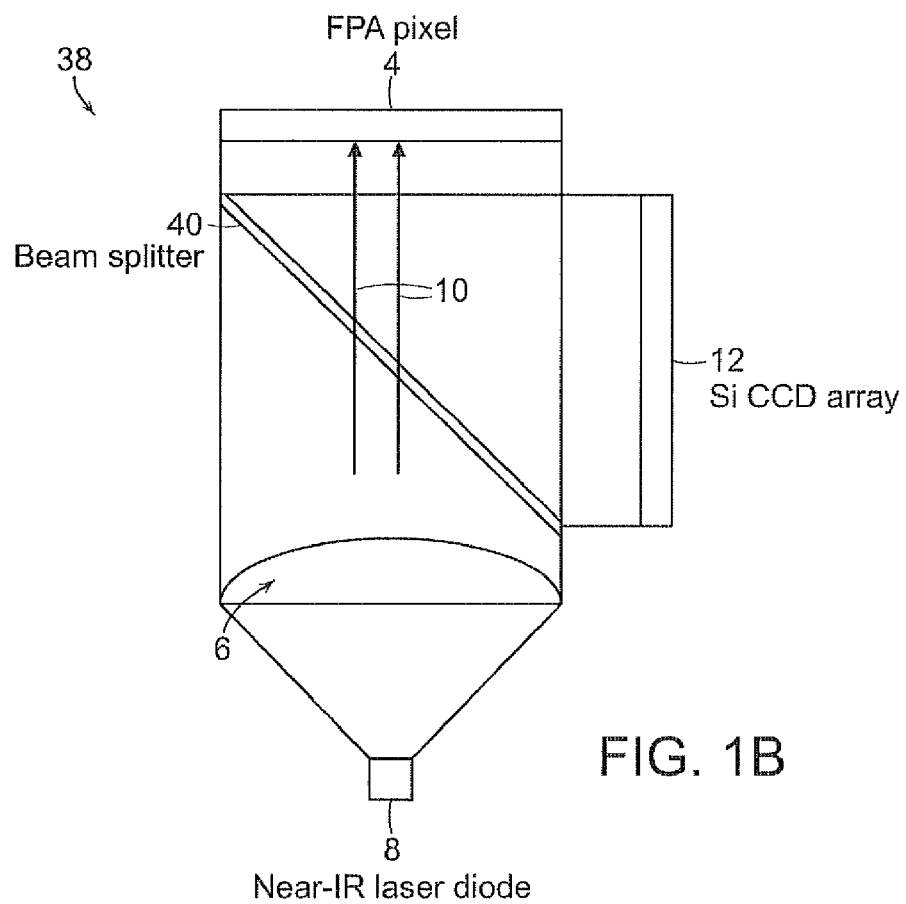

FIGS. 1A and 1B illustrate two optical designs 2, 38 for an SPP pixel array 4 that uses variations of reflected probing light to measure index changes resulting from incident infrared radiation. The SPP pixel array 4 is placed near the focal point of infrared optics producing IR radiation 10 and serves as the focal plane array for thermal image formation. The thermal image projected onto the SPP pixel array 4 results in the formation of a temperature map on the pixel array: the temperature is higher at locations with stronger incident radiation. The temperature map then leads to variations of near-IR or visible light reflectivities across the pixel array through coupling with SPP modes. Importantly, the substrate on which the FPA pixels are fabricated needs to be transparent to the incident infrared radiation detected by the pixels in the design shown in FIG. 1B.

Reflection of a collimated probing beam 6 (wavelength ranges from visible to near-IR depending on the specific pixel material and configuration) from a laser diode 8, which carries the temperature map information, is picked up by a silicon charge-coupled device (CCD) 12 and then the corresponding infrared/thermal image can be extracted from CCD 12 output after some simple image processing. In FIG. 1B, the extraction is accomplished using a beam splitter 40 that caries temperature map information to the CCD 12. Other techniques that either use angular interrogation (mechanically rotating CCD) or wavelength interrogation (spectrophotometry) for monitoring SPP coupling are also applicable for the inventive SPP FPA design.

Figure 2:
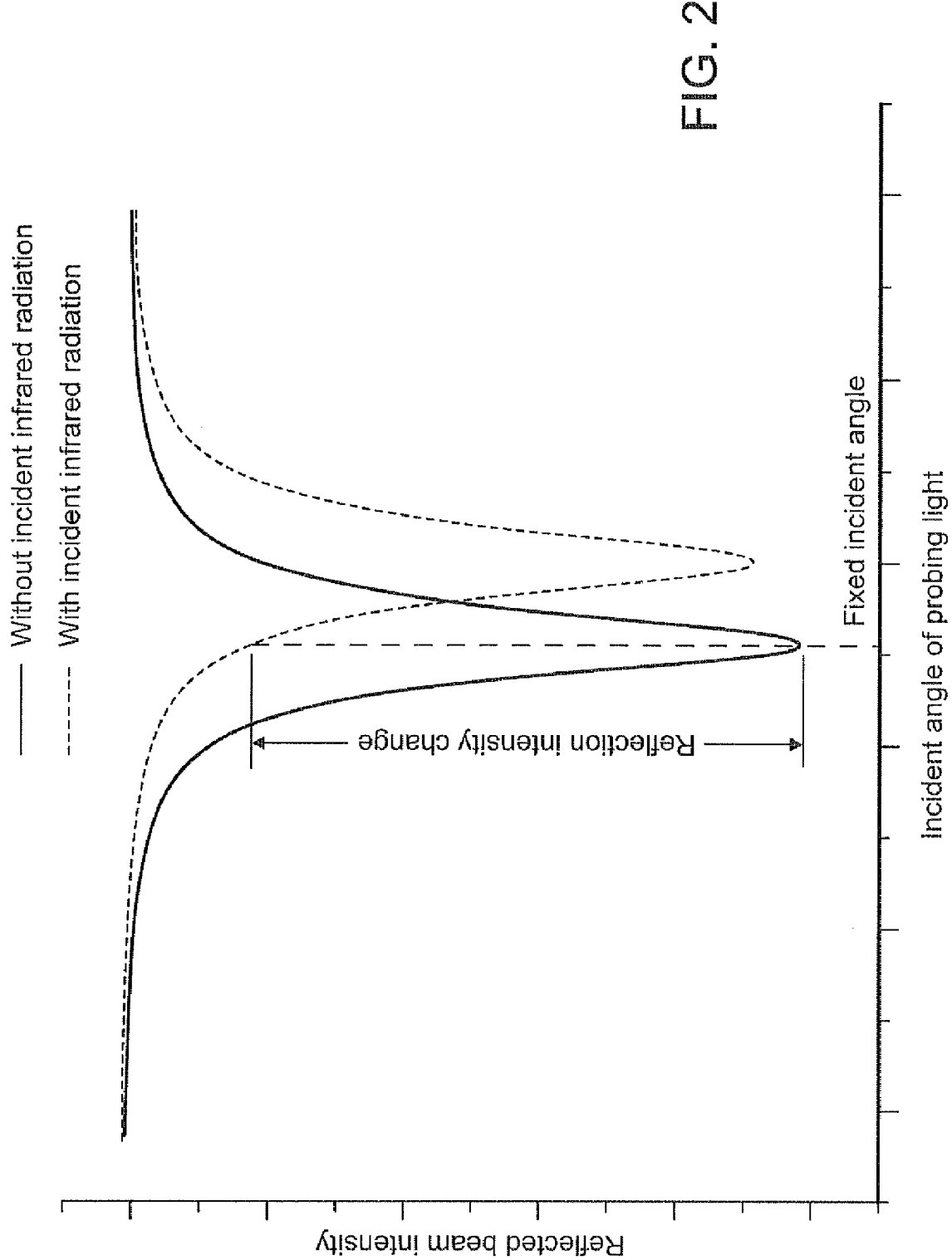
FIG. 2 is a graph illustrating the simulated response of the inventive SPP pixel.

FIG. 2 illustrates the simulated response of a SPP pixel. The dip on the reflectivity curve corresponds to effective coupling of probing light into SPP mode. When incident infrared radiation induces a refractive index change near the top metal layer, the position of the reflectivity dip is shifted to a different incident angle. In the detector configuration illustrated in FIG. 1, the incident angle of the probing light in fixed, and the index change due to infrared radiation is monitored through the reflection intensity change.

Figure 3:
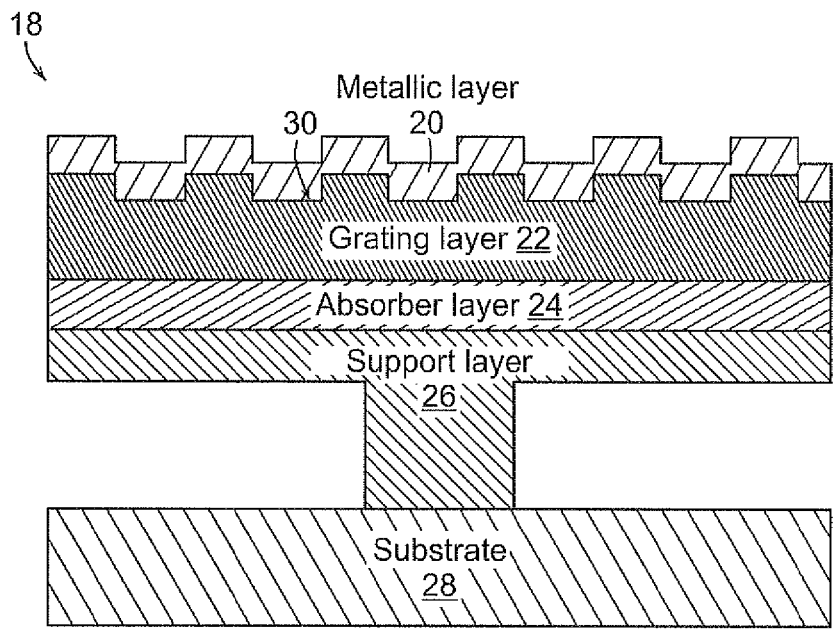
FIG. 3 is a schematic diagram illustrating the cross-section of the inventive SPP FPA pixel.

FIG. 3 schematically shows the cross-section of an SPP FPA pixel 18. In this specific embodiment, the pixel 18 is comprised of a multi-layer structure having a metal layer 20, a surface grating layer 22, an absorber layer 24 and a support layer 26. The gratings engraved on the metal layer 20 couple probing light into a SPP mode in the metal/grating interface 30. The layer 24 beneath the surface grating layer 22 serves as infrared absorber and the whole pixel structure 18 is suspended above the substrate to provide thermal isolation using the support layer 26. An infrared FPA is comprised of a planar array of such pixels.

Figure 4:
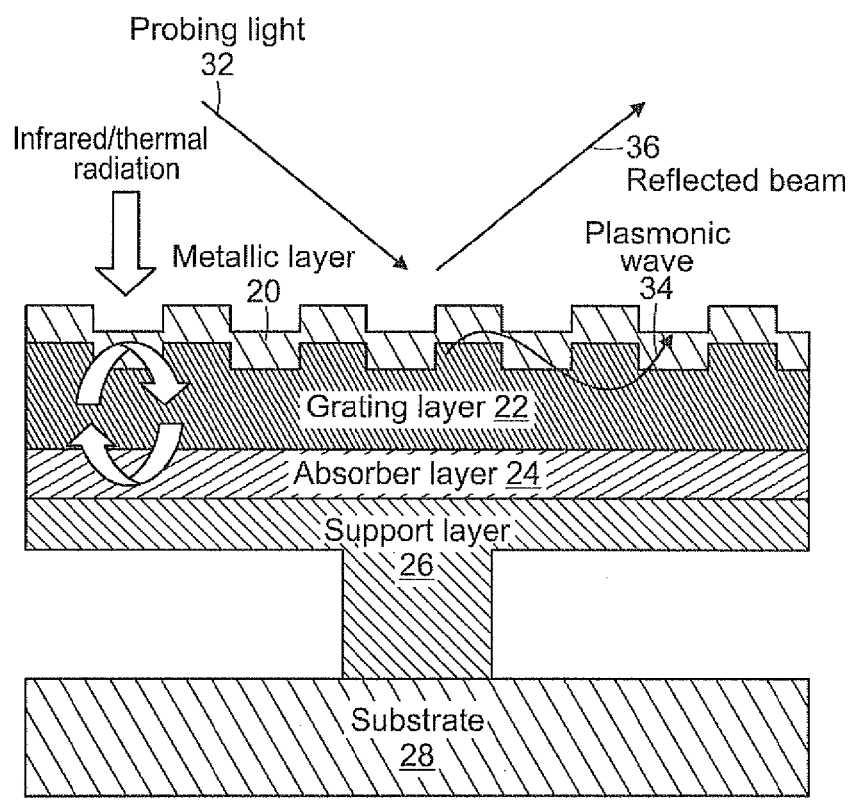
FIG. 4 is a schematic diagram illustrating the operations of the inventive SPP FPA pixel.

FIG. 4 illustrates the pixel operation when using the pixel structure 18 outlined in FIG. 3. The thin top metal layer 20, the grating layer 22 with appropriate thickness, and the absorber layer 24 can form a quarter-wavelength cavity that enhances infrared absorption. When index of the grating layer 22 changes due to thermo-optic effect, the coupling strength of probing light 32 into a SPP wave 34 also varies accordingly, this then leads to a measurable change of the reflected beam intensity 36. The probing light includes wavelengths between 2 and 25 μm.

Note other specific multi-layer structures and material choices can be used in accordance with the invention. Any infrared pixel design that involves the utilization of SPP coupling for thermo-optic radiation detection is within the scope of the invention. The top thin metal layer 20 serves to support the SPP mode/wave 34 at the metal/grating interface 30. A number of metals such as Au, Ag and Cu have been found to effectively support SPP propagation. Both smooth metal surface and corrugated metal surface (such as metal gratings) support SPP mode 34, and in the latter case the SPP mode is often specifically referred to as localized surface plasmon polariton (LSPP).

Gratings engraved on the grating layer 22 beneath the metal film helps to couple incident probing light 32 into SPP mode 34 by matching their in-plane wave vector. In order to facilitate coupling into SPP mode 34, the grating layer 22 is required to have relatively low refractive index, a requirement that can be satisfied by most polymers and dielectrics. The gratings can be patterned via deep ultraviolet (DUV) lithography, interference lithography or embossing/imprint technique in the case of polymer gratings. Besides processing flexibility, the advantage of using polymer as the grating layer 22 includes its high thermo-optic coefficient. In other embodiments of the invention grating layer can include a 1-D grating/photonic crystal or 2-D photonic crystal as well as utilize prism coupling. The absorber layer 24 beneath grating layer 22 serves to absorb incident infrared/thermal radiation to be detected. In principle, any material that is highly absorbing to infrared light with a wavelength range of interest may be used as the absorber material, and specifically in the case of a thermal IR detector, high resistivity metals such as TiN and NiCr are often employed for this application.

The thin top metal layer 20, the grating layer 22, and the absorber layer 24 can form a quarter-wavelength cavity that enhances infrared absorption by properly designing the grating layer 22 thickness. The resonant cavity structure reduces the absorber thickness and pixel thermal capacity, which improves the pixel sensitivity to infrared radiation and detector response speed. Finally, the whole pixel is isolated from its surrounding materials via a support structure 26. The structure 26 provides mechanical support and includes materials with good mechanical properties and low thermal conductivity, such as silicon nitride. Since the pixel structure 18 includes layers 20-24 that are made of amorphous or polycrystalline materials, the FPA 18 can in principle be fabricated on any substrate 28, which provides large flexibility for FPA design and cost reduction.

Figure 5:
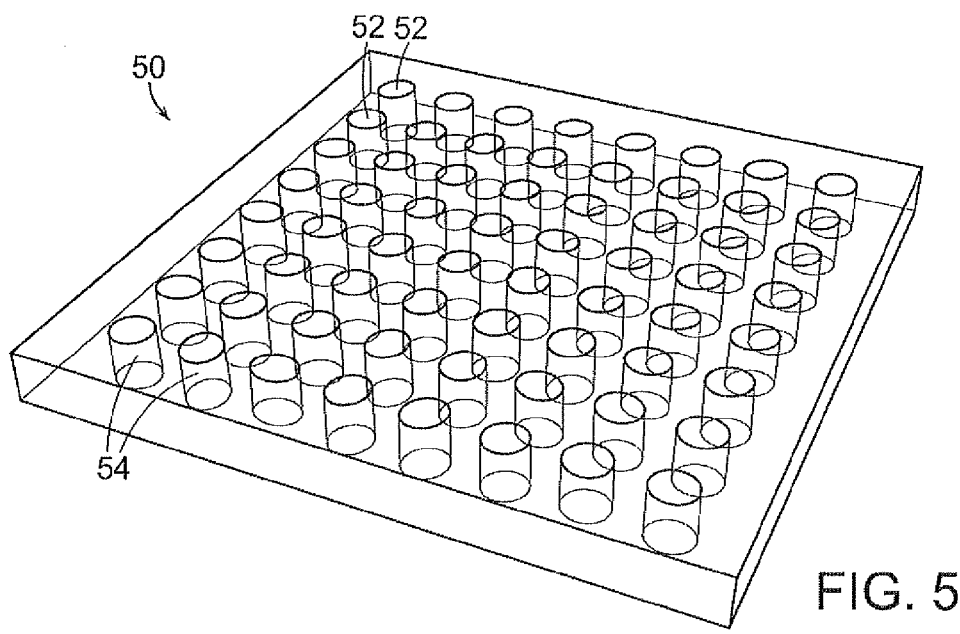
FIG. 5 is a schematic diagram showing a photonic crystal (PhC) slab with periodic hole arrays.
Figure 6:
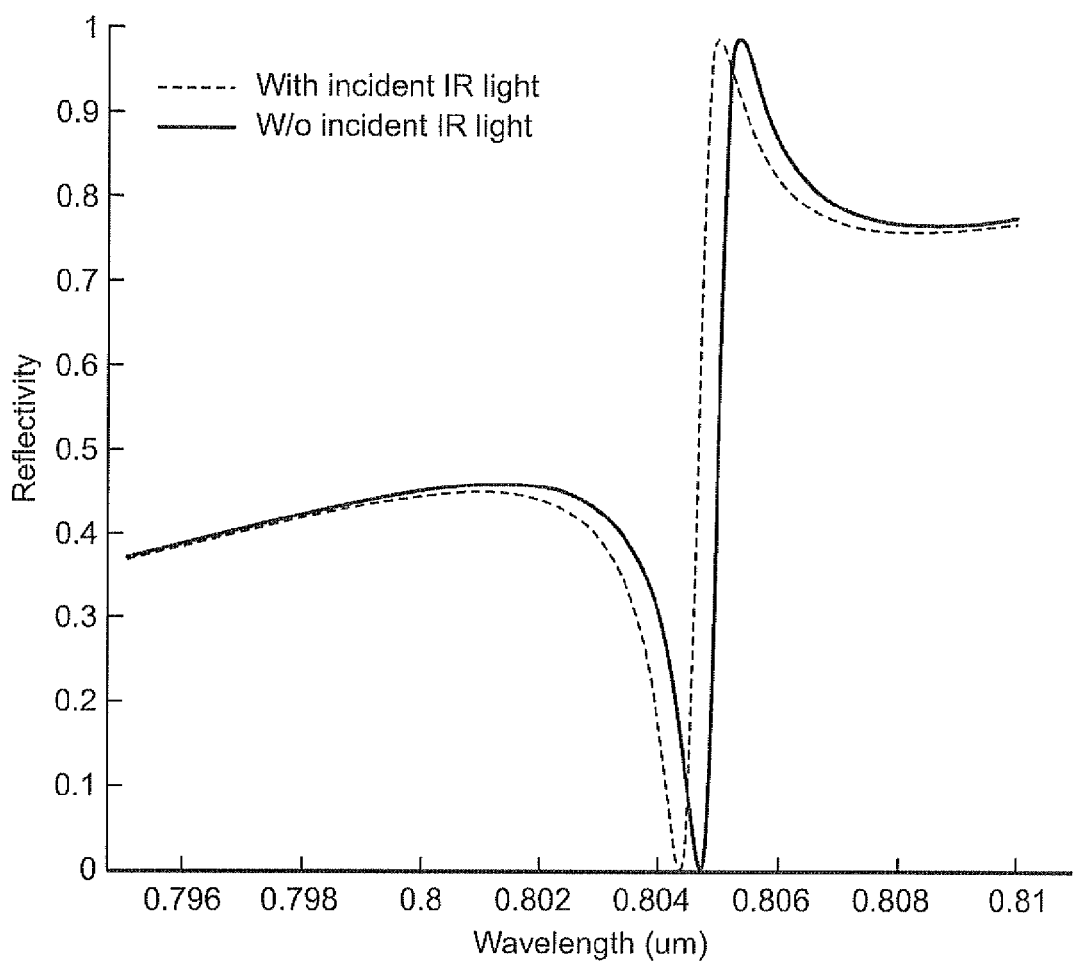
FIG. 6 is a graph illustrating the simulated response of the inventive photonic crystal slab pixel.

FIG. 5 shows a photonic crystal (PhC) slab structure 50 with periodic hole arrays 52 and rods 54. The PhC slab 50 is known in the art to have specific transmission properties shown in FIG. 6 to support the propagation of guided resonance modes.

Figure 7:
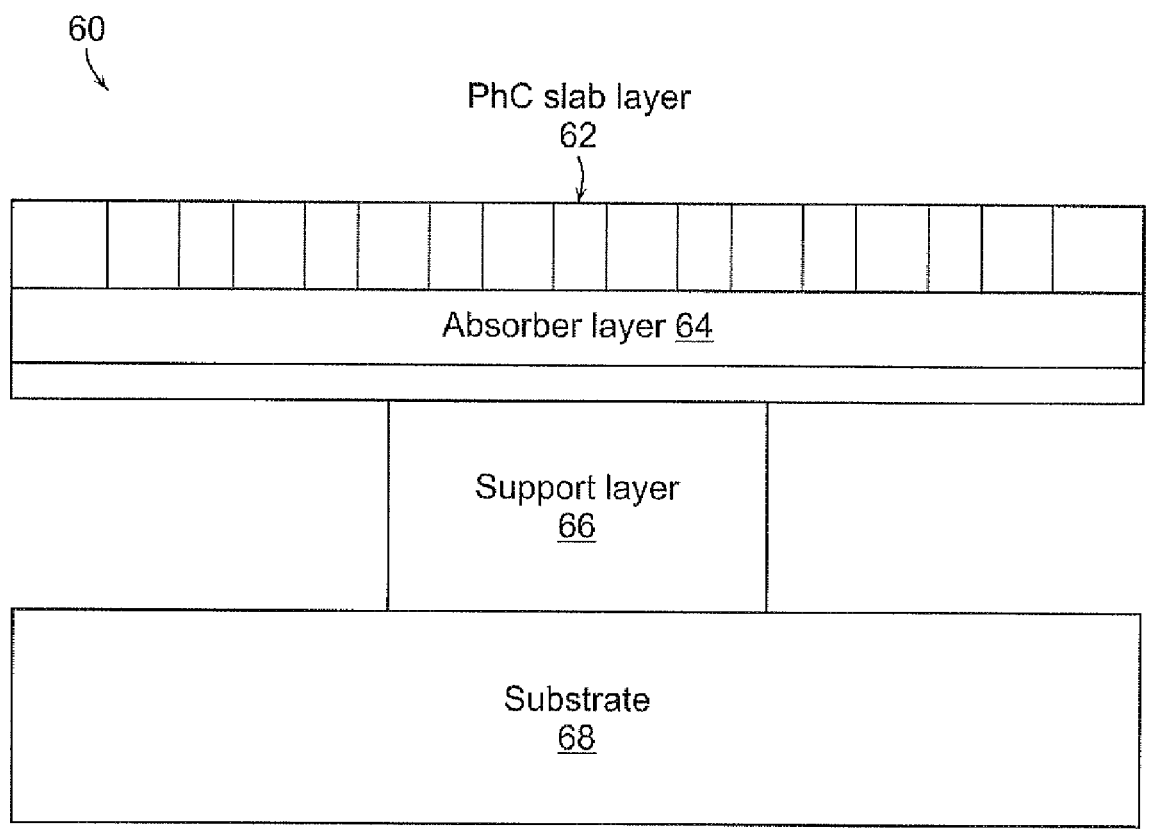
FIG. 7 is a schematic diagram illustrating the cross-section of the inventive photonic crystal slab FPA pixel.

FIG. 7 shows a PhC FPA 60 that includes a PhC slab structure 62 used in the formation of a thermal image. The PhC slab structure 62 includes a plurality of holes or rods to support the propagation of an in-plane guided resonance modes as shown in FIG. 5. An absorber layer 64 is positioned on or beneath the structure 62 for absorbing incident infrared/thermal radiation being detected. The pixel structure 60 is suspended above the substrate 68 to provide thermal isolation using the support layer 66.

The multi-layer pixel design described herein encompasses both infrared absorber and transducer in one integrated pixel structure. More generally, the invention covers thermo-optic infrared detector pixel designs that are comprised of separate IR absorber and transducer for measuring index changes using SPP coupling.

Although the present invention has been shown and described with respect to several preferred embodiments thereof, various changes, omissions and additions to the form and detail thereof, may be made therein, without departing from the spirit and scope of the invention.

What is claimed is:

1. A surface plasmon polariton (SPP) pixel structure comprising:
   a coupling structure that couples a probing light into a SPP mode by matching the in-plane wave vector by changing the refractive index of the coupling structure using thermo-optic effects to vary the coupling strength of said probing light into said SPP mode; and
   an absorber layer positioned on said coupling structure for absorbing incident infrared/thermal radiation being detected.

2. The SPP pixel structure of claim 1 further comprising a metallic layer comprising a plurality of first gratings for coupling said probing light signal to said coupling structure.

3. The SPP pixel structure of claim 1, wherein said coupling structure couples comprises grating coupling or prism coupling.

4. The SPP pixel structure of claim 1, wherein said coupling structure comprises low index materials.

5. The SPP pixel structure of claim 2, wherein said metallic layer, said coupling structure, and said absorber layer form a quarter-wavelength resonator cavity that enhances infrared absorption.

6. The SPP pixel structure of claim 1, wherein said absorber layer comprises TiN or NiCr.

7. The SPP pixel structure of claim 3, wherein said grating coupling comprises a 1-D grating/photonic crystal or 2-D photonic crystal.

8. The SPP pixel structure of claim 1, wherein said probing light comprises wavelengths between 2 and 25 µm.

9. The SPP pixel structure of claim 2 further comprising a supporting structure providing mechanical support for said metallic layer, coupling structure, and said absorber layer.

10. The SPP pixel structure of claim 1, said coupling structure comprises a photonic crystal (PhC) slab structure having a plurality of holes or rods to support the propagation of in-plane guided resonance modes.

11. A method of forming a surface plasmon polariton (SPP) pixel structure comprising:
    providing a metallic layer comprising a plurality of first gratings for coupling a probing light signal into a SPP mode;
    positioning a coupling structure on said metallic layer, said coupling structure further couples said probing light into said SPP mode by matching the in-plane wave vector by changing the refractive index of the coupling structure using thermo-optic effects to vary the coupling strength of said probing light into said SPP mode; and
    positioning an absorber layer on said coupling structure for absorbing incident infrared/thermal radiation being detected.

12. The method of claim 11 further comprising a metallic layer comprising a plurality of first gratings for coupling said probing light signal to said coupling structure.

13. The method of claim 11, wherein said coupling structure couples comprises grating coupling or prism coupling.

14. The method of claim 11, wherein said coupling structure comprises low index materials.

15. The method of claim 12, wherein said metallic layer, said coupling structure, and said absorber layer form a quarter-wavelength resonator cavity that enhances infrared absorption.

16. The method of claim 11, wherein said absorber layer comprises TiN or NiCr.

17. The method of claim 13, wherein said grating coupling comprises a 1-D grating/photonic crystal or 2-D photonic crystal.

18. The method of claim 1, wherein said probing light comprises wavelengths between 2 and 25 µm.

19. The method of claim 11 further comprising a supporting structure providing mechanical support for said metallic layer, coupling structure, and said absorber layer.

20. The method of claim 11, said coupling structure comprises a photonic crystal (PhC) slab structure having a plurality of holes or rods to support the propagation of in-plane guided resonance modes.

21. A surface plasmon polariton (SPP) focal plan array (FPA) comprising:
    a plurality of surface plasmon polariton (SPP) pixel structures used in the formation of a thermal image, each of said SPP pixel structure comprising:
        a coupling structure positioned that couples a probing light into a SPP mode by matching the in-plane wave vector by changing the refractive index of the coupling structure using thermo-optic effects to vary the coupling strength of said probing light into said SPP mode; and
        an absorber layer positioned on said coupling structure for absorbing incident infrared/thermal radiation being detected.

22. The SPP FPA of claim 21, further comprising a metallic layer comprising a plurality of first gratings for coupling said probing light signal to said coupling structure.

23. The SPP FPA of claim 21, said coupling structure comprises a photonic crystal (PhC) slab structure having a plurality of holes or rods to support the propagation of in-plane guided resonance modes.

24. The SPP FPA of claim 21, wherein said coupling structure comprises low index materials.

25. The SPP FPA of claim 22, wherein said metallic layer, said coupling structure, and said absorber layer form a quarter-wavelength resonator cavity that enhances infrared absorption.

* * * * *